United States Patent [19]
Hoops

[11] 3,991,471
[45] Nov. 16, 1976

[54] HUMIDIFYING PALATE

[76] Inventor: Donald F. Hoops, 2205 Paradise Road, Las Vegas, Nev. 89105

[22] Filed: July 14, 1975

[21] Appl. No.: 595,554

[52] U.S. Cl. .................................................. 32/1
[51] Int. Cl.² ......................................... A61C 19/00
[58] Field of Search ........... 128/132, 172, 261, 262, 128/269; 32/16, 1

[56] References Cited
UNITED STATES PATENTS 3,259,129  7/1966  Tepper .............................. 32/14 B
3,600,807  8/1971  Sipos .................................... 32/2

*Primary Examiner*—Robert Peshock
*Attorney, Agent, or Firm*—Edward J. Quirk

[57] ABSTRACT

A palatal appliance for maintaining humidity in the mouth and respiratory tract consists of a rigid plastic shell which substantially conforms to hard palate. The shell has a recess in the upper portion thereof to hold a sponge which can be saturated with liquid. Apertures extending through the floor of the recess allow the liquid to flow into the mouth at a controlled rate.

4 Claims, 4 Drawing Figures

HUMIDIFYING PALATE

BACKGROUND OF THE INVENTION

Many people have experienced the phenomenon of a dry mouth and throat under various circumstances. For example, athletes such as runners or long-distance skiers who have undergone a prolonged period of exertion and rapid breathing may not salivate sufficiently to keep the mouth moist. People subjected to high stress and tension may also experience these symptoms. In hot, dry climates, the existence of a dry mouth and respiratory tract is quite common; indeed, entertainers in Las Vegas often suffer from "Vegas throat," which is caused by breathing hot air having a very low humidity and which occasionally is sufficiently serious to require cancellation of a singing engagement.

In addition to causing discomfort, lack of moisture in the mouth and respiratory tract may cause extended irritation to delicate tissues, increasing the risks of infection and chronic problems such as sinus difficulties. Accordingly, it is useful to have a device which can maintain humidity in the mouth during periods of extended activity, such as skiing, golfing, or running, or for use in any activity in desert-type climates.

The use of artificial absorptive devices in the mouth for various purposes is well-known. For example, Pierce et al, U.S. Pat. No. 321,847 issued July 7, 1885 describes a full dental plate having a small absorptive strip of perfumed or medicated material fastened into the suction cavity thereof. This device is not suitable for use for humidification purposes, since the volume of absorptive material is very small and since the absorptive material does not have sufficient communication with the inside of the mouth to allow substantial flow of water to the mouth. In addition, the Pierce device is not easily and conveniently removable, since it consists basically of a full set of false teeth.

Other devices for releasing medicaments or perfumes into the mouth are shown in Sipos, U.S. Pat. No 3,600,807, issued Aug. 24, 1971, and Greenberg, U.S. Pat. No. 3,624,909, issued Dec. 7, 1971. Sipos discloses a plug-like removable insert which may be embedded in a false tooth or other dental apparatus, and which can absorb breath-freshening liquid. This device is also too small to serve as a humidifier. Greenberg teaches a resilient, horseshoe-shaped medicine applicator which fits over the teeth and which releases controlled amounts of medicine to the teeth and gums. This device could not be useful as a humidifier in most social situations since it covers the wearer's teeth.

Accordingly, it is an object of the invention to provide a device which fits into the mouth relatively unobtrusively and which contains an absorptive medium for holding a liquid for humidifying the mouth and respiratory tract. It is a further object to provide such a device which can be quickly and easily inserted and removed by the wearer, and which can be recharged simply by taking a drink of water. It is a further object of the invention to provide a device which will dispense small amounts of liquid into the mouth by application of slight upward pressure by the tongue of the wearer.

SUMMARY OF THE INVENTION

A palatal appliance for maintaining humidity in the mouth comprises a rigid plastic shell shaped to conform to the hard palate and having a shallow recess in the upper surface thereof, a sponge wedge adapted to fit into said recess having a volume of at least 0.6 cubic centimeters, and fastening means for holding the shell in place against the maxillary arch.

DETAILED DESCRIPTION OF THE INVENTION

Figure 1:
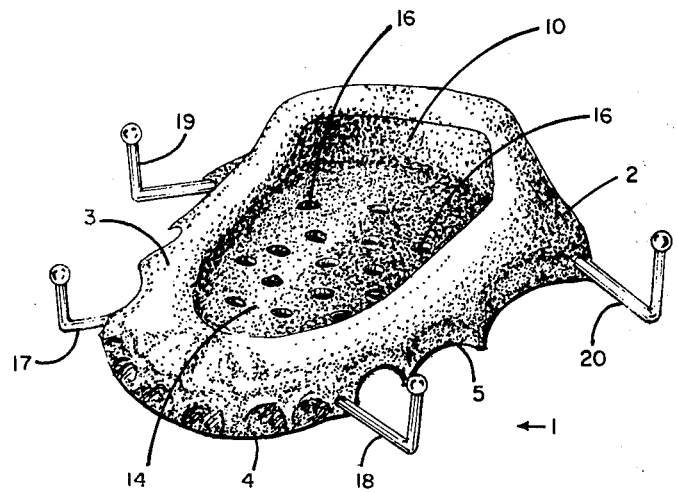
FIG. 1 is a top perspective view of a palatal humidifier of the invention without the sponge in place.
Figures 2, 3:
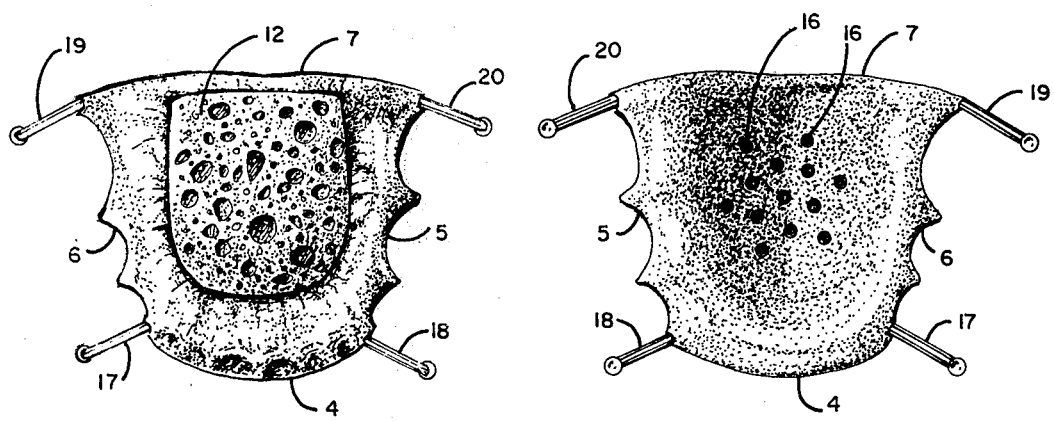
FIG. 2 is a top view of the humidifier with the sponge in place.
FIG. 3 is a bottom view of the device.

Referring to the drawings, plastic dental appliance 1 is adapted to conform to the hard palate in the roof of the mouth in a manner similar to an orthodontic retainer. The appliance consists of a custom-fit shell or base 2 designed to extend substantially across the roof of the wearer's mouth, with upper ledge portion 3 which extends around the periphery of the shell abutting the roof of the mouth. The periphery is defined by front edge 4 which rests behind the front teeth, side edges 5 and 6, and rear wall 7. The rear wall extends inside the mouth to a point just behind the first molar teeth on each side; if desired, the rear wall of the appliance may be extended further back into the mouth, e.g., to behind the second molar teeth, to accommodate a larger sponge.

A recess 10 having a substantially uniform depth of 2–3 millimeters is approximately centrally located on the upper side of the shell. The recess extends to within about 0.7 centimeter from front edge 4 and from side edges 5 and 6. Sponge wedge 12, which rests in the recess, is about 2 centimeters long, 1½ centimeters wide, and an average of about 3 millimeters thick. The size of the sponge wedge is generally as large as possible consistent with the comfort of the wearer, and may vary considerably with mouth size, in some cases reaching a thickness of up to about 5 millimeters. The sponge has a volume of at least 0.6 cc, preferably at least 0.8 cc, and still more preferably at least 1.0 cc. Larger sponge volumes, to 1.5 cc and even 2.0 cc may be tolerated by larger people but volumes greater than 2.0 cc are unnecessary for humidification and tend to become quite bulky. The sponge need not be uniform or regular in shape; indeed, depending on the shape of the mouth, the sponge may be desirably cut wedge-shaped, being thicker toward the rear of the mouth than at the front (see FIG. 4). The most important factor in sponge shape and size is the comfort of the wearer, and this must often be judged by trial and error.

Figure 4:
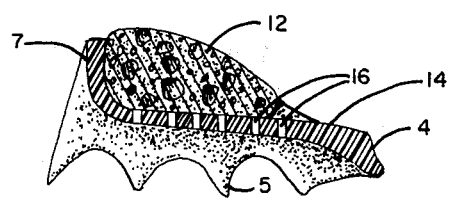
FIG. 4 is a cross-sectional side view of the device.

FIG. 4 shows a side section of the humidifier, showing the sponge cut to a wedge-shape to fit the roof of the wearer's mouth. The rear portion of the sponge extends slightly above the rear wall for reasons of comfort. Also, with this design the wearer need only press upwards on the bottom surface of the palate to compress the sponge slightly and release fluid.

The recess 10 is defined by walls which slope slightly inwardly and a floor 14 having a plurality of bores 16 having a diameter of about 1 mm. extending therethrough. The bores allow easy communication between the recess and the mouth of the wearer, such that fluid retained in the sponge can travel through the bores in the liquid or vapor phase. The sponge is preferably fit loosely into the recess, but may be fastened to the floor of the recess with a very small amount of an appropriate adhesive, e.g., a non-water-soluble glue. The floor of the device is about 1 mm in thickness.

FIG. 4 shows a bottom view of the appliance, with smooth surface 13 indicating the portion of the device which may contact the wearer's tongue when the device is in place.

The sponge wedge may be made from any suitable open or closed cell absorbent material such as latex, polystyrene, polyurethane, or polyester. Natural sponge may also be used. Open cell sponge, such as open cell flexible polyurethane foam, is preferred as having better absorptive properties. Any stable, non-degradable porous material having the ability to absorb water, and to release the water under slight pressure, may be used for the absorbent.

The bores or apertures 16 extending through the shell in the floor of the recess provide a convenient path for fluid or vapors to travel into the mouth of the wearer. The use of such apertures is preferred but is not essential, since the absorbed fluid can travel around the edges of the shell to the mouth. The type of apertures is not critical; for example, even a wire or plastic mesh may be used as a portion of the recess floor to provide communication between the upper and lower surfaces of the shell. In general, it is preferred to maintain the total area of the apertures to less than 30 square millimeters, still more preferably less than 20 square millimeters, in order to avoid rapid depletion of the absorbed liquid.

The shell is held in place by conventional ball clasps 17 and 18 at the forward portion and 19 and 20 at the rear of the shell. The front ball clasps are located to fit just behind the cuspid teeth, and the back clasps fit behind the first molar teeth on each side. When the appliance is in place, the clasp fits over the teeth and the ball tip on the end of the clasp is biased inward toward the space between the teeth, providing a firm fit of the appliance to the teeth. The location of the clasps is not critical, though fastening to teeth behind the first cuspids is preferred so that the clasps are less visible. The ball clasps are stainless steel wires, 040 gauge, which have a small rounded bead on the end. Any other conventional easily releasable fastening means, such as C-clasps, which hook around the molar teeth, or Akers clasps, may be used to hold the device up against the maxillary arch.

The palatal humidifier of the invention is fabricated by conventional techniques for making orthodontic retainers. First, a standard alginate impression of the maxillary arch is made. Then plaster or dental stone is poured into the impression to make a positive model of the arch. Dental setup wax, such as that manufactured by Miner Dental Products, is then cut to approximate the size of the sponge and is placed on the positive model at the location where the recess is desired. For medium grade wax slabs, which are about 1 mm thick, usually two or three thicknesses are required. The model is then painted with a separating medium, such as Liquid Foil Separator manufactured by Great Lakes Orthodontic Products, Inc., to keep the plastic from sticking to the model. Next, the ball clasp wires are bent to the appropriate shape, and the ball end of the clasp is adhered to the positive model with wax. Self-curing orthodontic acrylic resin is then poured over the model, surrounding and bonding the ball clasps to the acrylic and forming the shell. In about one-half hour, the acrylic cures to a hard plastic, and any excess material is trimmed away. The set up wax is then scooped away from the appliance, leaving the recess for the sponge wedge. The holes in the floor of the recess may be drilled with a standard electric drill. The sponge is cut to size with scissors and fit to the recess.

In use, the humidifying palate is easily slipped in place by inserting the shell in the wearer's mouth and pressing upwardly, snapping the ball clasps into place. The sponge may be saturated with fluid prior to insertion of the device, or may be saturated by the wearer taking a mouthfull of water and forcing the water into the sponge through the bores. While the device is in place, small amounts of fluid may be withdrawn from the sponge either through suction action of the inside of the mouth, or through application of a slight amount of upward pressure by the tongue on underside surface 13, compressing the sponge and squeezing a small amount of fluid through the apertures.

While the purpose of the device of the invention is to humidify the mouth in dry climates, it is possible to absorb fluids other than water in the device. For example, cough syrups or other liquids required to be dispensed into the mouth in relatively large volumes may be absorbed. Aqueous fluids are preferred, since the rate of evaporation is similar to water, for which the device is designed.

While the palatal device of the invention has been described with regard to a specific embodiment, various modifications within the scope and spirit of the invention will be apparent to those skilled in the art, and the invention should be considered to be defined and limited only by the following claims.

I claim:

1. A palatal appliance for maintaining humidity in the mouth of a wearer comprising:
   a rigid plastic shell having an upper surface shaped to fit the hard palate and a smooth lower surface, said upper surface having a shallow recess therein,
   an absorbent sponge wedge mounted in the recess and having a volume of at least 0.6 cubic centimeters, and
   fastening means carried by the shell for releasably attaching the shell to the hard palate of the wearer.

2. The palatal appliance of claim 1 wherein the recess has a plurality of apertures extending through the shell to allow passage of fluid from the sponge wedge into the mouth of the wearer.

3. The palatal appliance of claim 1 wherein the total area of the apertures is less than 30 square millimeters.

4. The palatal appliance of claim 1 wherein the fastening means comprise ball clasps.

* * * * *